(12) United States Patent
Filén

(10) Patent No.: US 10,227,660 B2
(45) Date of Patent: Mar. 12, 2019

(54) STRAND-INVASION BASED DNA AMPLIFICATION METHOD

(71) Applicant: ORION DIAGNOSTICA OY, Espoo (FI)

(72) Inventor: Sanna Filén, Kirkkonummi (FI)

(73) Assignee: Orion Diagnostica OY, Espoo (FI)

( * ) Notice: Subject to any disclaimer, the term of this patent is extended or adjusted under 35 U.S.C. 154(b) by 390 days.

(21) Appl. No.: 14/786,773

(22) PCT Filed: Apr. 23, 2014

(86) PCT No.: PCT/EP2014/058257
§ 371 (c)(1),
(2) Date: Oct. 23, 2015

(87) PCT Pub. No.: WO2014/173963
PCT Pub. Date: Oct. 30, 2014

(65) Prior Publication Data
US 2016/0102343 A1   Apr. 14, 2016

(30) Foreign Application Priority Data
Apr. 25, 2013  (EP) .................................... 13275100

(51) Int. Cl.
*C12P 19/34* (2006.01)
*C12Q 1/689* (2018.01)
*C12Q 1/6844* (2018.01)

(52) U.S. Cl.
CPC .......... *C12Q 1/689* (2013.01); *C12Q 1/6844* (2013.01); *C12Q 2600/158* (2013.01)

(58) Field of Classification Search
CPC ............ C12Q 1/6844; C12Q 2521/507; C12Q 2527/101; C12Q 2561/109; C12Q 1/689; C12Q 2600/158
USPC ...................................................... 435/91.2
See application file for complete search history.

(56) References Cited

U.S. PATENT DOCUMENTS

| 6,432,642 B1 | 8/2002 | Livak et al. |
| 6,596,486 B2 | 7/2003 | Frank-Kamenetskii et al. |
| 2005/0112631 A1 | 5/2005 | Piepenburg et al. |
| 2007/0054296 A1 | 3/2007 | Piepenburg et al. |

FOREIGN PATENT DOCUMENTS

| JP | 2006333785 | 12/2006 |
| KR | 20040032588 | 4/2004 |
| WO | 2001020035 A2 | 3/2001 |
| WO | WO 01/20035 | 3/2001 |
| WO | 2006051988 A1 | 5/2006 |
| WO | WO 2006/051988 | 5/2006 |
| WO | 2007096702 A2 | 8/2007 |
| WO | WO 2007/096702 | 8/2007 |
| WO | 2008035205 A2 | 3/2008 |
| WO | WO 2008/035205 | 3/2008 |
| WO | WO 2009/030031 | 3/2009 |
| WO | WO 2009/150467 | 12/2009 |
| WO | WO 2013/031973 | 3/2013 |

OTHER PUBLICATIONS

Sambol et al., Infect. Immun. 68 (10), 5480-5487 (Year: 2000).*
Lemee., Microbiology, 151, 3171-3180 (Year: 2005).*
Sauerborn et al., 18 (6), 1629 (Year: 1990).*
Demidov "PD-loops technology: PNA openers at work" Expert Rev. Mol. Diagn. 1 (3), 343-351 (2001).
Gill and Ghaemi "Nucleic Acid Isothermal Amplification Technologies—A Review" Nucleosides, Nucleotides and Nucleic Acids, 27:224-243, 2008.
Mori and Notomi "Loop-mediated isothermal amplification (LAMP): a rapid, accurate, and cost-effective diagnostic method for infectious diseases" J Infect Chemother (2009) 15:62-69.
Belanger et al. "Rapid detection of Clostridium difficile in feces by real-time PCR", Journal of Clinical Microbiology, 41(2): 730-34, 2003.
Braun et al. "Definition of the single integration site of the pathogenicity locus in Clostridium Difficile" Gene, 181(1-2): 29-38, 1996.
Carter et al. "The role of toxin A and toxin B in the virulence of Clostridium difficile" Trends in Microbiology, 20(1): 21-29, 2012.
Green et al. "Cloning and characterization of the cytotoxin L-encoding gene of clostridium sordellii: homology with clostridium difficile cytotoxin B", Gene, 161(1): 57-61, 1995.
International Preliminary Report on Patentability Issued in PCT/EP2014/058257, dated Oct. 27, 2015.
International Search Report and Written Opinion Issued in PCT/EP2014/058257, dated Jul. 18, 2014.
Lyras et al. "Toxin B is essential for virulence of Clostridium difficile" Nature, 458(7242): 1176-1179, 2009.
McMillin et al. "Molecular screening of Clostridium difficile toxins A and B genetic determinants and identification of mutant strains", FEMS Microbiology Letters, 62(1): 75-80, 1991.
McMillin et al. "Simultaneous detection of toxin A and toxin B genetic determinants of Clostridium difficile using the multiplex polymerase chain reaction" Canadian journal of microbiology, 38(1), 81-83, 1992.
Persson et al. "New multiplex PCR method for the detection of Clostridium difficile toxin A (tcdA) and toxin B (tcdB) and the binary toxin (cdtA/cdtB) genes applied to a Danish strain collection", Clinical Microbiology and Infection, 14(11): 1057-1064, 2008.
Popoff "Purification and characterization of Clostridium sordellii lethal toxin and cross-reactivity with Clostridium difficile cytotoxin" Infect. Immun., 55(1): 35-43, 1987.

(Continued)

Primary Examiner — Cynthia B Wilder
(74) Attorney, Agent, or Firm — Norton Rose Fulbright US LLP

(57) ABSTRACT

A method for detecting toxigenic *Clostridium difficile* (*C. difficile*) by strand-invasion based DNA amplification is provided, together with oligonucleotides, compositions and kits suitable for use in this method.

7 Claims, 6 Drawing Sheets

Specification includes a Sequence Listing.

(56) References Cited

OTHER PUBLICATIONS

Rupnik et al. "Comparison of toxinotyping and PCR ribotyping of Clostridium difficile strains and description of novel toxinotypes", *Microbiology*, 147: 439-447, 2001.
Von Eichel-Streiber et al. "Large clostridial cytotoxins—a family of glycosyltransferases modifying small GTP-binding proteins" *Trends in Microbiology*, 4: 375-382, 1996.
Wren et al. "Nucleotide sequence of Clostridium difficile toxin A gene fragment and detection of toxigenic strains by polymerase chain reactions" *FEMS Microbiology Letters*, 58(1): 1-6, 1990.
Lavery, P. E., and Kowalczykowski, S. C. "Enhancement of recA protein-promoted DNA strand exchange by volume-occupying agents" J. Biol. Chem. 267, 9307-9314, 1992.
Taylor A, et al. "Isothermal quadruplex priming amplification for DNA-based diagnostics. Biophysical Chemistry" (2013) 171: 1-8.
Lee D, et al. "Detection of genetically modified organisms (GMOs) using isothermal amplification of target DNA sequences." (2009) BMC Biotechnology 9: 7.
Euler M, et al. "Recombinase Polymerase Amplification Assay for Rapid Detection of Francisella tularensis." Journal of Clinical Microbiology (2012) 50:2234-2238.
Tong Y, et al. "Multiple strategies to improve sensitivity, speed and robustness of isothermal nucleic acid amplification for rapid pathogen detection." BMC Biotechnology (2011) 11: 50.
Hoser et al., "Strand Invasion Based Amplification (SIBA®): A Novel Isothermal DNA Amplification Technology Demonstrating High Specificity and Sensitivity for a Single Molecule of Target Analyte", *PLoS One*, 9(11): e112656, 2014.
Extended European Search Report issued in EP Application No. 13275100.9, dated Sep. 20, 2013.
Lalande, Valerie, et al; "Evaluation of a Loop-Mediated Isothermal Amplification assay for Diagnosis of Clostridium difficile Infections"; Journal of Clinical Microbiology, Jul. 2011, vol. 49, No. 7., p. 2714-2716.
Demidov, Vadim "PD-loop technology: PNA openers at work" Expert Rev. Mol. Diagn. 1(3), 343-351 (2001).
Demidov and Frank-Kamenetskii "PNA Openers and Their Applications" Methods in Molecular Biology, vol. 208: Peptide Nucleic Acids: Methods and Protocols, 2002, pp. 119-130.
Gill et al: "Nucleic acid isothermal amplification technologies—A review," Nucleosides, Nucleotides and Nucleic Acids, vol. 27, No. 3, Mar. 1, 2008, pp. 224-243, Taylor & Francis, Philadelphia, PA.
Mori and Yasuyoshi "Loop-mediated isothermal amplification (LAMP): a rapid, accurate, and cost-effective diagnostic method for infectious diseases", Journal of Infection and Chemotherapy, vol. 15, No. 2, Apr. 2009, pp. 52-69.

\* cited by examiner

STRAND-INVASION BASED DNA AMPLIFICATION METHOD

FIELD OF THE INVENTION

The invention relates to a method for detecting toxigenic *Clostridium difficile* (*C. difficile*) by strand-invasion based DNA amplification. The invention also relates to oligonucleotides, compositions and kits suitable for use in this method, and their use for detection of toxigenic *C. difficile*.

BACKGROUND TO THE INVENTION

Clostridia are gram-positive, spore forming anaerobic bacteria. Pathogenic Clostridia species produce protein toxins of which the group of large clostridial cytotoxins (LCTs) consists of very large toxins with high in vivo toxicity as well as high structural and sequence homology (von Eichel-Streiber et al., 1996). *C. difficile* toxins A and B are the major cause of *C. difficile* pathogenicity. For a long time toxin A was considered the major virulence factor, but increasing amount of evidence is showing that in fact toxin B plays a major role in *C. difficile* infections (Lyras et al., 2009; Carter et al., 2012).

*C. difficile* toxin A and B are encoded by genes tcdA and tcdB, respectively, and the genes are located in a ~19.6 kb pathogenicity locus (PaLoc). The PaLoc contains also two regulatory genes, namely tcdC and tcdR, which act as negative and positive regulators, respectively, of toxin expression. tcdE, also included in the PaLoc, encodes for a holin-like protein necessary for toxin A and B secretion. In non-toxigenic strains the PaLoc is replaced by a 115 bp sequence (Braun et al., 1996). DNA amplification has been used for detection of toxigenic *C. difficile* strains (Wren et al., 1990; McMillin et al., 1991; McMillin et al., 1992).

An isothermal DNA amplification process relying on an upstream primer, a downstream primer, and a strand invasion system is described in WO 2009/150467.

SUMMARY OF THE INVENTION

The present invention relates to detection of a target nucleic acid sequence of toxigenic *C. difficile*, to allow for the presence of toxigenic *C. difficile* in a sample to be determined. The method of the invention uses an upstream primer, a downstream primer, and a strand invasion oligonucleotide, each comprising a region complementary to said target nucleic acid sequence. In combination, the primers and strand invasion oligonucleotide provide for amplification of the target nucleic acid sequence. The strand invasion oligonucleotide renders at least a portion of the target nucleic acid sequence single-stranded to allow the binding of the upstream primer and downstream primer, thereby permitting amplification of DNA. Typically, the amplification is performed under isothermal conditions, without a requirement for thermal denaturation of double-stranded DNA.

If amplification of the target nucleic acid sequence is detected, this is indicative that a toxigenic strain of the target pathogen *C. difficile* is present in the sample, and not a non-toxigenic, non-pathogenic strain of *C. difficile*, or other *Clostridium* species. The inventors have shown that the method of the invention allows for highly specific and sensitive detection of different target nucleic acid sequences of toxigenic *C. difficile*.

The invention provides a method for detecting a target nucleic acid sequence of toxigenic *C. difficile* in a sample, said method comprising contacting said sample with at least one upstream primer, at least one downstream primer and at least one strand invasion oligonucleotide under conditions promoting amplification of said target nucleic acid sequence, wherein each said primer and said oligonucleotide comprises a region complementary to said target nucleic acid sequence; and wherein said strand invasion oligonucleotide renders at least a portion of the target nucleic acid sequence single-stranded to allow the binding of said upstream primer and a downstream primer.

The invention further provides a composition and a kit, each comprising at least two oligonucleotides selected from (a) an upstream primer, (b) a downstream primer and (c) a strand invasion oligonucleotide, wherein:

(I) the upstream primer is an oligonucleotide of less than 30 nucleotides in length comprising the sequence of SEQ ID NO: 2 or a variant thereof, the downstream primer is an oligonucleotide of less than 30 nucleotides in length comprising the sequence of SEQ ID NO: 3 or a variant thereof, and the strand invasion oligonucleotide is an oligonucleotide of greater than 30 nucleotides in length comprising the sequence of SEQ ID NO: 4 or a variant thereof, and further comprising one or more modified nucleotides in its 3'region; or (II) the upstream primer is an oligonucleotide of less than 30 nucleotides in length comprising the sequence of SEQ ID NO: 7 or a variant thereof, the downstream primer is an oligonucleotide of less than 30 nucleotides in length comprising the sequence of SEQ ID NO: 8 or a variant thereof, and the strand invasion oligonucleotide is an oligonucleotide of greater than 30 nucleotides in length comprising the sequence of SEQ ID NO: 9 or a variant thereof, and further comprising one or more modified nucleotides in its 3'region.

The invention further provides use of an upstream primer, a downstream primer, and a strand invasion oligonucleotide, each as defined in (I) above, or each as defined in (II) above in a method for detection of *C. difficile*.

The invention additionally provides a method for diagnosis of a *C. difficile* infection in a subject, comprising carrying out a method for detecting a target nucleic acid sequence of toxigenic *C. difficile* according to the invention in a sample from said subject.

were detected from NTC reaction whereas a specific amplification product was detected from tcdB reaction in which 10 000 cp *C. difficile* gDNA was used as template.

Figure 2A:
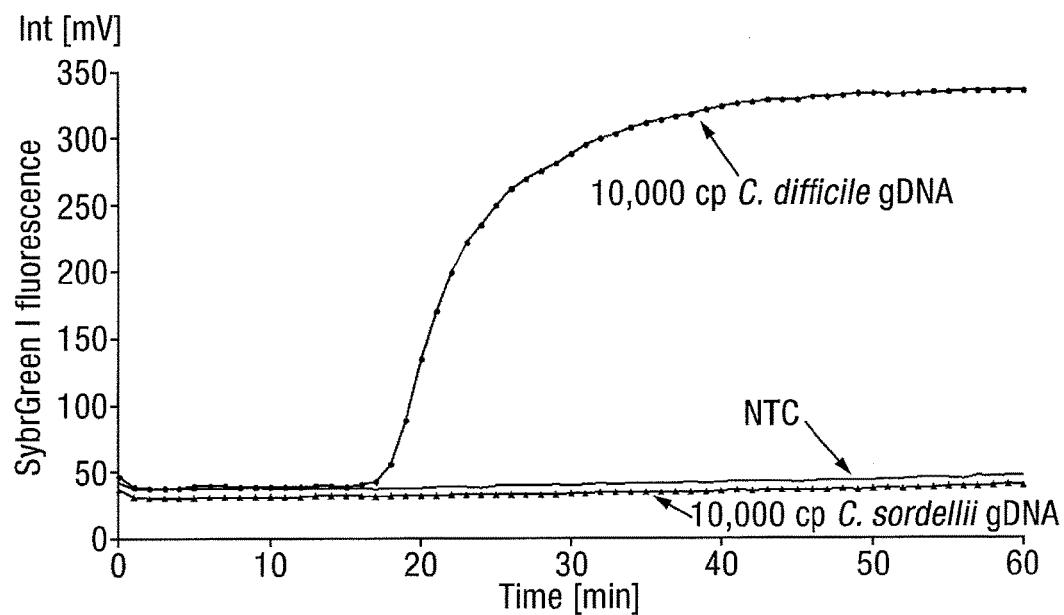
Figure 2B:
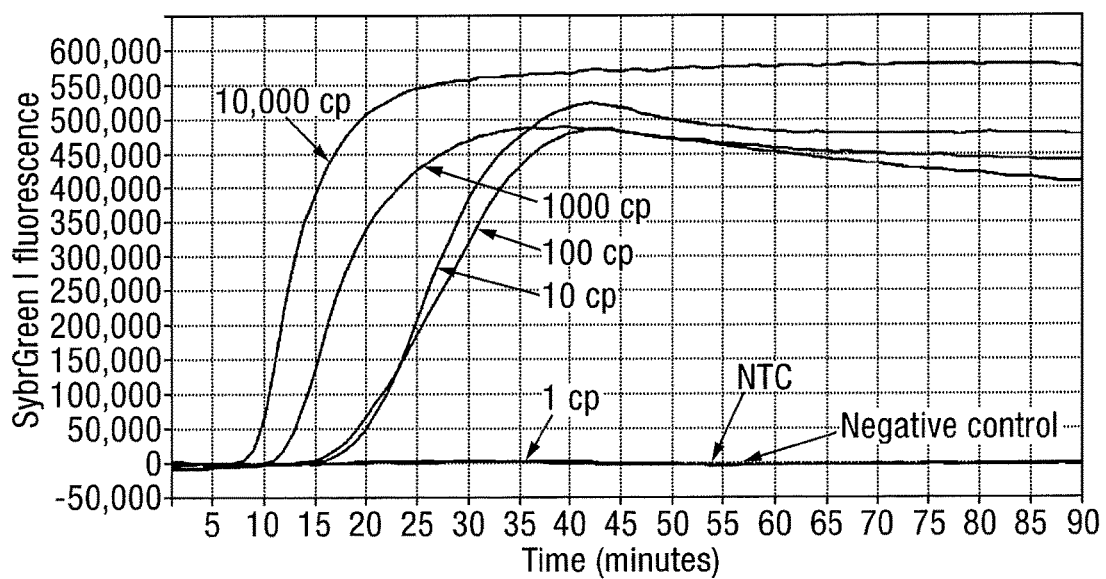

FIG. 2 shows: (A) Specificity of tcdB assay. X-axis: time (minutes), Y-axis: SybrGreen I fluorescence (fluorescence intensity, millivolts, mV). 10 000 cp *C. difficile* BAA-1382 (630) and 10 000 cp *C. sordellii* ATCC 9714 gDNA were used as templates for tcdB reaction. Only *C. difficile* gDNA was amplified and detected. No template control (NTC) shows no amplification. (B) Sensitivity of tcdB assay. X-axis: time (minutes), Y-axis: SybrGreen I fluorescence (fluorescence intensity, arbitrary units). Sensitivity of tcdB assay was determined using a dilution series of *C. difficile* BAA-1382 (630) gDNA as template. 10-10 000 cp *C. difficile* gDNA showed amplification measured by increase in SybrGreen I fluorescence whereas no template control (NTC) and negative control reactions did not amplify. All reactions were performed in the presence of 0.5 ng/μl herring sperm DNA.

FIG. 3 shows: (A) Inclusivity of tcdB assay. X-axis: time (minutes), Y-axis: SybrGreen I fluorescence (fluorescence intensity, arbitrary units)]. 2 ng gDNA isolated from pure cultures of *C. difficile* toxinotypes 0, III, VIII and X was used as template for tcdB assay. NTC (no template control). All tested toxinotypes gave a positive amplification result. (B) Inclusivity of tcdB assay for a panel of toxinotypes, details as in (A) above, but using 2 ng gDNA isolated from pure cultures of *C. difficile* Toxinotypes 0, I, II, IIIa, IIIb, IIIc, IV, V, VI, VII, VIII, IX, X, XIa, XIb, XII, XIII, XIV, XV, XVI, XVII, XVIII; XIX, XX, XXI; XXII; XXIII; XXIV, XXV, XXVI, XXVII, XVIII, XXIX, XXX, XXXI, XXXII and XXXIII. Only two toxinotypes, namely XIa and XIb gave a negative amplification result. (C) Melt curve analysis of tcdB reactions with gDNA template isolated from different *C. difficile* toxinotypes as in (A). X-axis: Temperature (degrees Centigrade), Y-axis: (−d(fluorescence)/d(temperature), arbitrary units). All *C. difficile* toxinotypes showed amplification of a single amplicon. No template control (NTC) shows no amplification. (D) Melt curve analysis, details as in (C) above, for the panel of toxinotypes of (B). Melt curve analysis also showed no amplification for toxinotypes XIa and XIb.

Figure 4A:
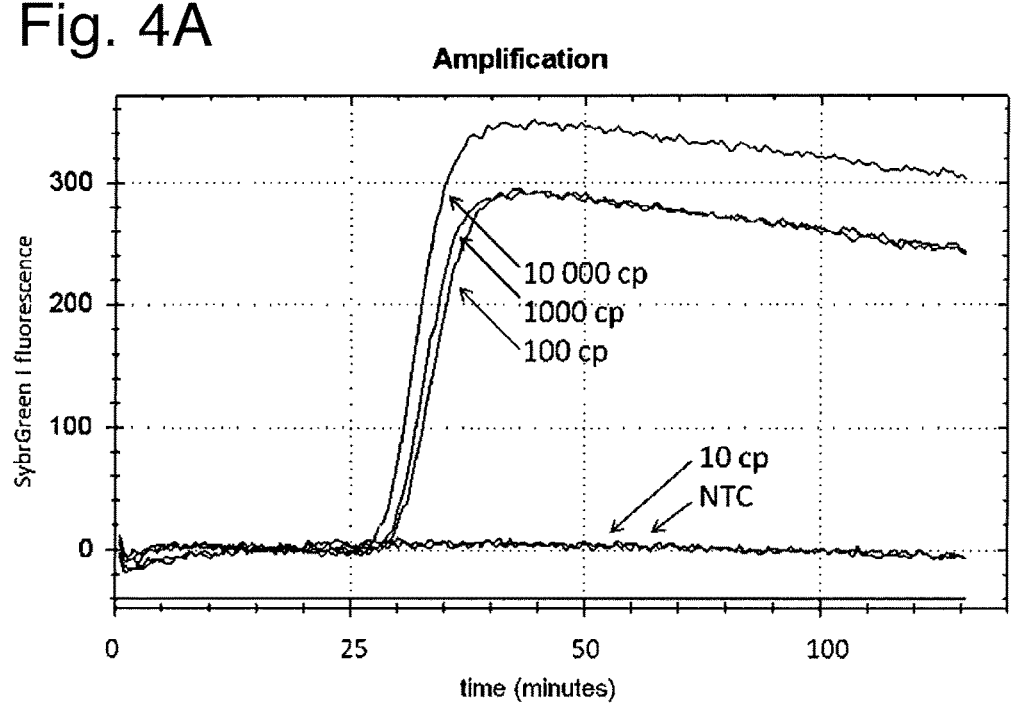

FIG. 4 shows: (A) tcdA assay amplification plot. SybrGreen I was used for detection and fluorescence was measured with real-time PCR instrument. X-axis: time (minutes), Y-axis: SybrGreen I fluorescence (fluorescence intensity, arbitrary units). Amplification was observed with 100-10 000 cp/reaction *C. difficile* BAA-1382 (630) gDNA and no amplification observed in the presence of 0-10 cp/reaction *C. difficile* gDNA and with no template control (NTC). (B) tcdA assay melt curve analysis. X-axis: Temperature (degrees Centigrade), Y-axis: (−d(fluorescence)/d (temperature)), arbitrary units). The melt curve analysis shows amplification of a single specific amplicon. No template control (NTC) shows no amplification.

DESCRIPTION OF THE SEQUENCES

SEQ ID NO: 1 is the nucleotide sequence of a tcdB target region.
SEQ ID NO:2 is the nucleotide sequence of a tcdB forward primer.
SEQ ID NO:3 is the nucleotide sequence of a tcdB reverse primer.
SEQ ID NO: 4 is the nucleotide sequence of a tcdB strand invading oligonucleotide.

SEQ ID NO: 5 is the nucleotide sequence of a modified tcdB strand invading oligonucleotide.
SEQ ID NO: 6 is the nucleotide sequence of a tcdA target region.
SEQ ID NO: 7 is the nucleotide sequence of a tcdA forward primer.
SEQ ID NO: 8 is the nucleotide sequence of a tcdA reverse primer.
SEQ ID NO: 9 is the nucleotide sequence of a tcdA strand invading oligonucleotide.
SEQ ID NO: 10 is the nucleotide sequence of a modified tcdA strand invading oligonucleotide.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting. In addition as used in this specification and the appended claims, the singular forms "a", "an", and "the" include plural referents unless the content clearly dictates otherwise. Thus, for example, reference to "a polypeptide" includes two or more such polypeptides, and the like. All publications, patents and patent applications cited herein, whether supra or infra, are hereby incorporated by reference in their entirety.

Method of Detection of Toxigenic *C. difficile* in a Sample Sample

Commonly, the sample is a clinical sample, for example a sample obtained from a patient suspected of having, or having an infection by *C. difficile*. However, any sample can be used, provided that nucleic acid can be obtained or derived from the sample. Thus, reference samples of particular *C. difficile* strains, or environmental samples may be used in the present invention. Suitable types of clinical sample vary according to the particular type of infection that is present, or suspected of being present in a subject. The sample may be blood, plasma, serum, urine or a stool sample. In a preferred embodiment, the sample is a stool sample. The stool sample may be taken from a subject having a gastrointestinal tract infection. The infection may be present in a patient having diarrhoea.

In preferred embodiments, the samples are taken from animal subjects, such as mammalian subjects. The samples will commonly be taken from human subjects, but the present invention is also applicable in general to domestic animals, livestock, birds and fish. For example, the invention may be applied in a veterinary or agricultural setting.

The sample comprises nucleic acid which may be DNA or RNA. If the nucleic acid is present in the sample in a suitable form allowing for detection according to the invention, the sample may be used directly. However, typically, nucleic acid is derived, obtained or extracted from the sample. Methods for processing samples containing nucleic acids, extracting nucleic acids and/or purifying nucleic acids for use in detection methods are well-known in the art. Total nucleic acid may be isolated or DNA and RNA may be isolated separately.

Typically, a sample is processed in an appropriate manner such that nucleic acid is provided in a convenient form for contacting with the primers and strand invasion oligonucleotide. Where the nucleic acid is DNA, the DNA is typically provided in double-stranded form. Where the nucleic acid is an RNA, it is typically converted to cDNA using reverse transcriptase or a polymerase with reverse transcriptase activity. RNA may be useful for bacterial detection, owing to the very large number of ribosomes present in bacterial cells which effectively amplify the concentration of target sequences.

Target Nucleic Acid Sequence

The target nucleic acid sequence is a region of the *C. difficile* genome (or amplicon) suitable for use in specific detection of toxigenic *C. difficile*. This allows for a highly qualitative, unambiguous determination of the presence of toxigenic *C. difficile* in the sample, even if closely related organisms exist. The selection of specific target nucleic acid sequences in toxigenic strains of a specific pathogen, and the consequent design of primer and strand invasion oligonucleotides for detection of those sequences is an important consideration. Examples of appropriate sequences are provided herein.

Typically, the target nucleic acid sequence will be unique to the *C. difficile* genome. The target nucleic acid sequence will thus typically differ from any homologous nucleic acid sequence in a related species, for example in a homologous *Clostridium* species. Typically, the target nucleic acid sequence will comprise several mismatches with a homologous nucleic acid sequence in a related species. Preferably, the target nucleic acid sequence is not present in a *Clostridium* species other than *C. difficile* that harbours genes for large clostridial toxins. The target nucleic acid sequence is preferably not present in *C. sordellii* and/or *C. novyi*. The target nucleic acid sequence typically allows for specific detection of *C. difficile* from a sample containing *C. difficile* and *C. sordellii* and/or *C. novyi*.

The target nucleic acid sequence typically has good inclusivity for different *C. difficile* toxinotypes, and thus is typically present and can be detected in more than one *C. difficile* toxinotype. Preferably, the target nucleic acid sequence is inclusive for at least three, more preferably at least five, at least seven, at least ten, at least fifteen, at least twenty, at least twenty five, at least thirty, at least thirty five, most optimally for all *C. difficile* toxinotypes. *C. difficile* toxinotypes include Toxinotypes 0, I, II, IIIa, IIIb, Inc, IV, V, VI, VII, VIII, IX, X, XIa, XIb, XII, XIII, XIV, XV, XVI, XVII, XVIII; XIX, XX, XXI; XXII; XXIII; XXIV, XXV, XXVI, XXVII, XVIII, XXIX, XXX, XXXI, XXXII and XXXIII, and any further toxinotypes described in the art or existing in nature. Typically, the target nucleic acid sequence is inclusive for *C. difficile* toxinotypes found to be of clinical relevance in disorders associated with *C. difficile* infection.

The target nucleic acid sequence typically has a higher GC content than the average GC content of the *C. difficile* genome, which is 29.1% for *C. difficile* reference strain 630. The target nucleic acid sequence may have a GC content of at least 30%, more preferably at least 31%, at least 32% or at least 33%. Where the target nucleic acid sequence is present in the tcdA or tcdB gene, the average GC content of these genes is 27%, and so the preferred GC contents above are also higher compared to the average for these genes. The GC content of the target nucleic acid sequence is also selected with regard to the requirement for binding of primers and melting of the target sequence under the isothermal temperature conditions used.

The target nucleic acid sequence or amplicon is of a sufficient length to provide for specific detection of toxigenic *C. difficile* and for hybridisation of the upstream and downstream primers and strand invasion oligonucleotide in a suitable manner to different portions of the target sequence. Preferably, the amplicon is at least 45 nucleotides in length, more preferably at least 50, at least 55 or at least 60 nucleotides in length, as measured from the 5' site of binding of the upstream primer to the 5' site of binding of the downstream primer.

The target nucleic acid sequence may be present in any region of the *C. difficile* genome, provided it has the necessary characteristics for specific detection of toxigenic *C. difficile* as discussed above. The target nucleic acid sequence may be present in a noncoding DNA region specific to toxigenic *C. difficile* or a coding region specific to toxigenic *C. difficile*. The target nucleic sequence may be present in the pathogenicity locus of *C. difficile*. Preferably, the target nucleic acid sequence is present in the tcdA gene or the tcdB gene of *C. difficile*. Other suitable target genes may include the tcdC, tcdE, tcdR genes within PaLoc or binary toxin genes of *C. difficile*. Sequences are available at the listed accession numbers for the *Clostridium difficile* 630 complete genome (GenBank: AM180355.1), tcdA gene (AM180355.1: 795843-803975, tcdB gene (AM180355.1: 787393-794493).

The target nucleic acid sequence preferably comprises SEQ ID NO: 1 or a variant thereof (for detection of tcdA) or SEQ ID NO: 6 or a variant thereof (for detection of tcdB). It should be understood that the target nucleic acid sequence is a duplex which comprises a sense strand representing SEQ ID NO:1 or a variant thereof, or SEQ ID NO: 6 or a variant thereof, and a complementary anti-sense strand. The upstream and downstream primers used to amplify the target nucleic acid sequence bind to opposing strands of this duplex.

The target nucleic acid sequence may comprise a naturally occurring variant sequence of SEQ ID NO:1 or SEQ ID NO:6 which is present in a different toxinotype to reference strain *C. difficile* 630. Naturally occurring variants of SEQ ID NO: 1 or SEQ ID NO: 6 are found in the known sequences of different *C. difficile* toxinotypes, and for instance the corresponding sequence in some known toxinotypes comprises 1, 2 or 3 mismatches with the sequence of SEQ ID NO:1. Not yet sequenced toxinotypes may also comprise mismatches with respect to SEQ ID NO:1 or SEQ ID NO: 6. The inventors have surprisingly shown that the method of the invention is inclusive for detection of a wide range of toxinotypes even in the existence of such mismatches.

Variants of SEQ ID NO: 1 or SEQ ID NO: 6 may comprise a region which is partly or full complementary to at least 35 contiguous nucleotides, more typically at least 40, preferably at least 45 or at least 50 contiguous nucleotides of SEQ ID NO: 1 or SEQ ID NO: 6. The variants may comprise a region which has 1, 2, 3, 4, 5, 6, 7, 8, 9, 10, 11, 12 or more mismatches (substitutions) with respect to a region of the corresponding original target sequence of SEQ ID NO: 1 or SEQ ID NO: 6. Thus, for instance the variants may comprise a region of at least 35 nucleotides in length which has 1, 2, 3, 4, 5, or 6 mismatches, such as 1-3 or 1-5 mismatches, to a corresponding region of at least 35 contiguous nucleotides of the corresponding original target sequence. The variants may comprise a region of at least 40, 45, or 50 nucleotides in length which has 1, 2, 3, 4, 5, 6, 7, 8, 9 or 10, such as 1-5 or 1-8 mismatches to a corresponding region of an equivalent length in the corresponding original target sequence. Any mismatches in the variant sequence may be at least 2, at least 4, at least 5, or at least 10 nucleotides apart.

Alternatively, the variants may comprise a region of at least 35, 40, or 45 nucleotides in length which is in full complementarity with the original target sequence.

Most preferably, the target nucleic acid sequence comprises SEQ ID NO: 1 or SEQ ID NO: 6 or consists of SEQ ID NO: 1 or SEQ ID NO: 6 and a complementary antisense strand.

More than one target nucleic acid sequence may be detected in a method of the invention, by providing two or more sets of upstream primer, downstream primer and strand invasion oligonucleotide, each set adapted for detection of a different target nucleic acid sequence. For example, a method of the invention may detect both tcdB and tcdA.

Upstream and Downstream Primers

Suitable upstream and downstream primers are selected based on the target nucleic acid sequence of interest, and having regard to the site of binding of the strand invasion oligonucleotide that renders at least a portion of the target nucleic acid sequence single-stranded to allow the binding of the upstream primer and downstream primer.

The upstream and downstream primers comprise a sequence that is partly or fully complementary to the target and optionally a 5' and/or 3' flanking non-complementary sequence. Alternatively, the upstream and downstream primers may consist entirely of partly or fully complementary sequence to the target. The length of the primer sequence that is complementary to the target is sufficient to provide specific hybridisation to the target nucleic acid sequence. The length of complementary sequence is typically at least 10 nucleotides, more preferably at least 15, at least 16, or at least 17 nucleotides. The length of complementary sequence may be 10-25, 15-25, 10-30 or 15-30 nucleotides.

It should be understood that the above sequence lengths refer to portions of the primers which may be partly or fully complementary to the target nucleic acid sequence. Mismatches may be present between the primers and the target sequence at particular positions while still allowing for specific amplification and detection of the target sequence, in particular having regard to the combined use of upstream and downstream primers and a strand invasion oligonucleotide to achieve amplification. There may be 1, 2, 3, 4 or 5 mismatches between the complementary region of the primer and the corresponding region of the target sequence.

Preferably, the primer is designed to allow for specific detection of toxigenic *C. difficile*. Thus, the primer typically specifically or selectively hybridises to a complementary sequence found only in toxigenic *C. difficile*. However, the primer may also hybridise to other sequences, such as sequences found in other *Clostridium* species, provided that when used in combination with the second primer and strand invasion oligonucleotide, specific amplification of a sequence found only in toxigenic *C. difficile* is obtained.

Specific or selective hybridisation refers to the binding of a primer only to a particular nucleotide sequence under given conditions, when that sequence is present in a nucleic acid in a sample, such as a complex biological mixture including total cellular and foreign DNA or RNA. Appropriate hybridisation conditions are known in the art. See for example, Sambrook, Fritsche and Maniatis "Molecular Cloning: A Laboratory Manual", 2nd Ed. Cold Spring Harbor Press (1989), which is hereby incorporated by reference in its entirety. Appropriate hybridisation conditions are also provided in the Examples below. As is known to the skilled person, appropriate hybridisation conditions may vary depending on the length of a probe and its base composition. Hybridisation is typically performed at the same temperature as amplification, and thus also depends on the activity profile of the polymerase and recombinase enzymes employed.

Typically the upstream and downstream primer will be less than 30 nucleotides in total in length, more preferably less than 25 nucleotides in length, such as 15 to 25, or 15 to 23 nucleotides in length. It is particularly preferred that primers of less than 30 nucleotides in length are used where a recombinase is used for strand invasion. The primers are not capable of acting as substrates for recombinases.

The upstream (or forward) primer binds to the 5' region of one strand of the duplex target nucleic acid sequence, at a position proximal or overlapping with the 5' binding site of the strand invasion oligonucleotide. The downstream (or reverse) primer binds to the 5' region of the opposing strand of the duplex target nucleic acid sequence to the upstream primer, at a position proximal or overlapping with the 3' binding site of the strand invasion oligonucleotide. The 5' binding sites of the upstream and downstream primers are typically at least 45 nucleotides, more preferably at least 50, at least 55 or at least 60 nucleotides apart on the duplex target sequence.

The upstream and/or downstream primer may have a region of sequence overlap with the sequence of the strand invasion oligonucleotide. The region of sequence overlap is typically 1-8 nucleotides in length, and may be at least 5 or at least 6 nucleotides in length. The downstream primer may also have a region of sequence overlap of 1-8 nucleotides in length with the sequence of the strand invasion oligonucleotide.

Alternatively, there may be no sequence overlap between the upstream and/or downstream primer and the strand invasion oligonucleotide, with the primer binding instead at a position that is proximal in the target sequence to the binding site of the strand invasion oligonucleotide.

Where a primer binds proximal to the strand invasion oligonucleotide, typically there is 25 nucleotides or less, more preferably 20 nucleotides or less, 15 nucleotides or less, or 10 nucleotides or less between the relevant binding site of the strand invasion oligonucleotide and the 5' end of the primer. This ensures that the primer is able to hybridise to the single-stranded region created by binding of the strand invasion oligonucleotide.

Specific examples of suitable upstream and downstream primers for binding of target nucleotide sequences in the *C. difficile* tcdA and tcdB genes are provided herein. Preferred upstream and downstream primers for detection of the tcdB target sequence of SEQ ID NO:1 are the primers of SEQ ID NOs 2 and 3, or variants thereof. Preferred upstream and downstream primers for detection of the tcdA target sequence of SEQ ID NO: 6 are the primers of SEQ ID NOs 7 and 8, or variants thereof.

Variants of SEQ ID NOs 2, 3, 7 and 8 may be oligonucleotides of up to 30 nucleotides in length comprising a region which is partly or fully complementary to at least 10 contiguous nucleotides of the corresponding original primer sequence of SEQ ID NO: 2, 3, 7 or 8. Preferably, said variants will comprise a region which is partly or fully complementary to at least 11, 12, 13, 14 or 15 contiguous nucleotides of the corresponding original primer sequence of SEQ ID NO: 2, 3, 7 or 8. Where the original primer sequence is longer than 16 nucleotides in length, such as up to 21 nucleotides in length (SEQ ID NO:2) the variants may correspondingly comprise a region which is partly or fully complementary to 16, 17, 18, 19 or 20 contiguous nucleotides thereof.

The above variants may comprise a region which has 1, 2, 3, 4, or 5 mismatches (substitutions) with respect to the corresponding region of the original primer sequence (and thus the target sequence) and is partly complementary thereto. Thus, for instance, the variants may comprise a region of at least 10 nucleotides in length which has 1, 2, or 3 mismatches, such as 1 or 2 mismatches to a corresponding region of at least ten contiguous nucleotides of the corresponding original primer sequence. The variants may comprise a region of at least 13, 14 or 15 nucleotides in length which has 1, 2, 3, 4 or 5 mismatches, such as 1-3 mismatches to a corresponding region of an equivalent length in the corresponding original primer sequence. Any mismatches in the variant primer sequence may be at least 2, at least 4, at least 5, or at least 10 nucleotides apart.

Alternatively, the variants may comprise a region of at least 10, 11, 12, 13, 14 or 15 nucleotides in length which is in full complementarity with the original primer sequence.

Variants of SEQ ID NOs 2, 3, 7 and 8 may also be oligonucleotides of up to 30 nucleotides in length which have at least 70% sequence identity to the sequence of the corresponding original primer sequence, preferably at least 75%, at least 80%, more preferably at least 85%, at least 90%, at least 95% sequence identity.

Additionally, the variant primers may comprise a 5' or 3' flanking nucleotide sequence from the tcdA or tcdB gene with respect to the binding region of the original primers, such as 5-10 nucleotides from the 5' flanking region and/or 3-region. The variant primers may additionally comprise sequence unrelated to the target sequence.

Any upstream or downstream primer used in the invention may comprise one or more modified nucleotides and/or a detectable label, for example a fluorescent dye.

Strand Invasion Oligonucleotide

A suitable strand invasion oligonucleotide is selected based on the target nucleic acid sequence of interest, and having regard to the site of binding of the upstream and downstream primers and the requirement for the strand invasion oligonucleotide to render the target nucleic acid sequence single-stranded in the relevant regions to allow for the binding of the upstream primer and downstream primer.

The strand invasion oligonucleotide comprises a sequence that is complementary to the target and optionally additional flanking non-complementary sequence(s). The length of the sequence that is complementary to the target may be determined by the skilled person empirically and is sufficient to provide for efficient strand invasion of the target nucleic acid sequence, optionally under isothermal conditions. The complementary sequence may comprise RNA-DNA complementary base pairing and modified nucleotides. Typically, the length of complementary sequence is at least 25 or at least 27 nucleotides, typically at least 30 nucleotides, such as least 32, at least 33 or at least 35 nucleotides, more preferably at least 36, 37, 38, 39 or 40 nucleotides in length or greater. The length of complementary sequence may be 30-50, 32-50, 35-50, 40-50, 35 to 48, 35 to 46, 38 to 45 or 40 to 45 nucleotides in length.

It should be understood that the above sequence lengths refer to a portion of the strand invasion oligonucleotide which may be partly or fully complementary to the target nucleic acid sequence. Mismatches may be present between the strand invasion oligonucleotide and the target sequence at particular positions while still allowing for specific amplification and detection of the target sequence, in particular having regard to the combined use of upstream and downstream primers and a strand invasion oligonucleotide to achieve amplification. There may be 1, 2, 3, 4, 5, 6, 7, or 8 mismatches between the complementary region of the strand invasion oligonucleotide and the corresponding region of the target sequence, depending on the total length of complementary sequence.

Preferably, the complementary sequence of the strand invasion oligonucleotide is designed to allow for specific detection of toxigenic *C. difficile*. Thus, the strand invasion oligonucleotide preferably specifically or selectively hybridises to a complementary sequence found only in toxigenic *C. difficile*. However, the strand invasion oligonucleotide may also hybridise to other sequences, such as sequences found in other *Clostridium* species, provided that when used in combination with the primers, specific amplification of a sequence found only in toxigenic *C. difficile* is obtained.

The complementary sequence of the strand invasion oligonucleotide hybridises to a portion of the target sequence intervening the binding regions for the upstream and downstream primers (and typically overlapping with one or more thereof). The strand invasion oligonucleotide may have a region of overlap of 1-8 nucleotides, such as a region of at least 5 or at least 6 nucleotides in length, with the upstream and/or downstream primers.

The 5' portion of the complementary sequence of the strand invasion oligonucleotide typically binds within 25 nucleotides or less, more preferably 20 nucleotides or less from the 5' boundary of the duplex target nucleotide sequence to be melted (the amplicon).

The strand invasion oligonucleotide optionally further comprises non-complementary sequence region(s) to the target that flank the complementary sequence region. The strand invasion oligonucleotide may comprise a non-complementary 5' region which may be of any nucleotide sequence. The 5' non-complementary region is typically at least 3 nucleotides in length, more typically at least 6, at least 8, preferably at least 10, at least 12 or at least 14 nucleotides in length. The 5' non-complementary region may assist binding of recombinase. The strand invasion oligonucleotide may comprise a 3' non-complementary region typically of 1-3 nucleotides in length which comprises nucleotides which block polymerase extension such as invdT.

The strand invasion oligonucleotide is typically at least 30 nucleotides in length where a recombinase is used in conjunction with the oligonucleotide. The strand invasion oligonucleotide is preferably at least 35, at least 40 or at least 45 nucleotides in length, more preferably at least 50, and may be at least 55 nucleotides in length or greater. The strand invasion oligonucleotide may be 40-70, 45-70, 45-70, 50-70, 55-70, 45-65, 50-65, 50-60 or 55-65 nucleotides in length.

Typically the strand invasion oligonucleotide has a non-extendible 3'terminus, such that it cannot serve as a substrate for DNA amplification, and the target sequence is then only amplified on the further binding of the specific upstream and downstream primers. This avoids formation of non-specific amplification products. The strand invasion oligonucleotide may comprise one, two, three, four, five, six, seven, eight or more modified nucleotides in its 3'region, such as in the 10-15 or 10-20 nucleotides from the 3'terminus. The strand-invasion oligonucleotide may comprise a 3' modification of the 3'terminal nucleotide, and may be a dideoxynucleotide, or comprise a 3'amino-allyl group, a 3'carbon spacer, 3'phosphate, 3'biotin, 3'sialyl, or 3'thiol. The 3' nucleotide may be a nucleotide incorporated in a reversed orientation by a 3'-3' linkage. Alternatively or additionally, the 3' region of the strand-invasion oligonucleotide may comprise nucleotides with poor substrate capability for DNA polymerases, such as PNA (peptide nucleic acid) nucleotides, LNA (locked nucleic acid), 2'-5' linked DNA or 2'-O-methyl RNA, or combinations thereof.

Where the strand-invasion oligonucleotide is a PNA oligomer comprised wholly of PNA, such an oligonucleotide can destabilise and invade duplex DNA in the absence of a recombinase enzyme. Thus, where a PNA oligonucleotide is used, the methods of the invention may be performed without presence of a recombinase enzyme.

Specific examples of suitable strand invasion oligonucleotides for target nucleotide sequences in the *C. difficile* tcdA and tcdB genes are provided herein. A preferred strand invasion oligonucleotide for detection of the tcdB target sequence of SEQ ID NO: 1 is SEQ ID NO: 4. A particularly preferred strand invasion oligonucleotide is a modified derivative of SEQ ID NO: 4, most preferably SEQ ID NO: 5. A preferred strand invasion oligonucleotide for detection of the tcdA target sequence of SEQ ID NO: 6 is SEQ ID NO: 9. A particularly preferred strand invasion oligonucleotide is a modified derivative of SEQ ID NO: 9, most preferably SEQ ID NO: 10.

As discussed above, it is preferred that a strand invasion oligonucleotide used in the invention comprises one or more modified oligonucleotides in its 3'region to block its use as a polymerase substrate. Thus, a modified derivative of SEQ ID NO: 4 or 9 may comprise one, two, three, four, five, six, seven, eight or more modified nucleotides in its 3'region, typically in the 10-15 or 10-20 nucleotides from the 3'terminus. The modifications may be selected from any of those discussed above. The modified derivative may be a PNA oligomer of corresponding sequence to SEQ ID NO: 4 or 9.

In addition to modified derivatives of SEQ ID NOs 4 and 9, variant strand invasion oligonucleotides may be used.

Variants of SEQ ID NOs 4 and 9 are typically oligonucleotides of greater than 30 nucleotides, more preferably at least 35, at least 40, or at least 45 nucleotides in length, comprising a region which is partly or fully complementary to at least 30 contiguous nucleotides of the corresponding original target-complementary sequence present in SEQ ID NO: 4 or 9. Preferably, said variants will comprise a region which is partly or fully complementary to at least 32, 35, 37, 40, 42 or 45 contiguous nucleotides of the target-complementary sequence present in SEQ ID NO: 4 or 9.

The above variants may comprise a region which has 1, 2, 3, 4, 5, 6, 7 or 8 mismatches (substitutions) with respect to the corresponding target-complementary region of the original strand invasion oligonucleotide of SEQ ID NO: 4 or 9 (and thus the target sequence) and thus is partly complementary thereto. Thus, for instance, the variants may comprise a region of at least 30 nucleotides in length which has 1, 2, 3, or 4, such as 1-4 or 1-3 mismatches to a corresponding region of at least 40 contiguous nucleotides of the corresponding original strand invasion oligonucleotide. The variants may comprise a region of at least 35, 40, 42, or 45 nucleotides in length which has 1, 2, 3, 4, 5 or 6, such as 1-5, or 1-3 mismatches to a corresponding region of an equivalent length in the corresponding original strand invasion oligonucleotide. Any mismatches in the variant strand invasion oligonucleotide sequence may be at least 2, at least 4, at least 5, or at least 10 nucleotides apart.

Alternatively, the variants may comprise a region of at least 32, 35, 37, 40, 42 or 45 nucleotides in length which is in full complementarity with the target-complementary region of the original strand invasion oligonucleotide.

Variants of SEQ ID NOs 4 and 9 may also be oligonucleotides of greater than 30 nucleotides in length comprising a target-complementary region which has at least 70% sequence identity to the target-complementary sequence of the corresponding original strand invasion oligonucleotide, preferably at least 75%, at least 80%, more preferably at least 85%, at least 90%, at least 95% sequence identity.

Additionally, the variant strand invasion oligonucleotides may comprise additional sequence complementary to the 5' or 3' flanking nucleotide sequence of the tcdA or tcdB gene with respect to the binding region of the original strand invasion oligonucleotide, such as 5-10 or 5-15 nucleotides from the 5' flanking region and/or 3-region.

The remaining sequence of the variant strand invasion oligonucleotides is typically unrelated to the target sequence, and also typically unrelated to the original strand invasion oligonucleotide.

The variant strand invasion oligonucleotides further comprise one or more modified oligonucleotides in their 3'region such as, two, three, four, five, six, seven, eight or more modified nucleotides, which may be in the 10-15 or 10-20 nucleotides from the 3'terminus The modifications may be selected from any of those discussed above.

A strand invasion oligonucleotide of the invention may further comprise a detectable label, for example a fluorescent dye.

Amplification of the Target Nucleic Acid Sequence

The nucleic acid derived from the sample is contacted with the upstream and downstream primers and the strand invasion oligonucleotide for detection purposes, under conditions promoting amplification of the target nucleic acid sequence.

Such conditions typically comprise the presence of a DNA polymerase enzyme. Suitable conditions include any conditions used to provide for activity of polymerase enzymes known in the art.

The conditions typically include the presence of all four dNTPs, dATP, dTTP, dCTP and dGTP or analogues thereof, suitable buffering agents/pH and other factors which are required for enzyme performance or stability. The conditions may include the presence of detergents and stabilising agents. The temperature used is typically isothermal, i.e constant throughout the amplification process. The temperature used typically depends on the nature of the polymerase enzyme and other enzyme components, and also reflects the hybridisation temperature required for the primers and strand invasion oligonucleotides. Where Bsu polymerase is used, a suitable temperature is 40 degrees centigrade.

The polymerase used typically has strand-displacement activity. The term "strand displacement" is used herein to describe the ability of a DNA polymerase, optionally in conjunction with accessory proteins, to displace complementary strands on encountering a region of double stranded DNA during DNA synthesis. Suitable DNA polymerases include polI from *E. coli, B. subtilis*, or *B. stearothermophilus*, and functional fragments or variants thereof, and T4 and T7 DNA polymerases and functional fragments or variants thereof. A preferred polymerase is Bsu DNA polymerase or a functional fragment or variant thereof.

The conditions may further comprise the presence of a recombinase. Any recombinase system may be used in the method of the invention. The recombinase system may be of prokaryotic or eukaryotic origin, and may be bacterial, yeast, phage, or mammalian. The recombinase may polymerise onto a single-stranded oligonucleotide in the 5'-3' or 3'-5; direction. The recombinase may be derived from a myoviridae phage, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2. In a preferred embodiment, the T4 recombinase UvsX (Accession number: P04529) or a functional variant or fragment thereof is used. The Rad systems of eukaryotes or the recA-Reco system of *E. coli* or other prokaryotic systems may also be used.

The conditions may further comprise the presence of recombinase accessory proteins, such as single-stranded binding protein (e.g. gp32, accession number P03695) and recombinase loading agent (e.g. UvsY, accession number NP_049799.2). In a preferred embodiment, the conditions comprise the presence of the T4 gp32, UvsX and UvsY proteins.

The recombinase (such as UvsX), and where used the recombinase loading agent (such as UvsY) and single stranded DNA binding protein (such as gp32), can each be native, hybrid or mutant proteins from the same or different myoviridae phage sources. A native protein may be a wild type or natural variant of a protein.

The conditions may further comprise other factors used to enhance the efficiency of the recombinase such as compounds used to control DNA interactions, for example proline, DMSO or crowding agents which are known to enhance loading of recombinases onto DNA (Lavery P et. Al JBC 1992, 26713, 9307-9314; WO2008/035205).

The conditions may also comprise the presence of an ATP regeneration system. Various ATP regeneration systems are known to the person skilled in the art, and include glycolytic enzymes. Suitable components of an ATP regeneration system may include one or more of phosphocreatine, creatine kinase, myokinase, pyrophosphatase, sucrose and sucrose phosporylase. The conditions may further comprise the presence of ATP.

Additional components such as magnesium ions, DTT or other reducing agents, salts, BSA/PEG or other crowding agents may also be included.

The various components described above, inclusive of the primers and strand invasion oligonucleotide, may be provided in varying concentrations to provide for DNA amplification. The skilled person can select suitable working concentrations of the various components in practice.

Detection of Presence of Amplified DNA

The presence of amplified DNA resulting from the contacting of the target nucleic acid sequence with the primers and strand invasion oligonucleotide under conditions promoting DNA amplification may be monitored by any suitable means.

One or both of the primers, or the strand invasion oligonucleotide may incorporate a label or other detectable moiety. Any label or detectable moiety may be used. Examples of suitable labels include radioisotopes or fluorescent moieties, and FRET pairs of a fluorophore and acceptor moiety. Alternatively, or additionally one or more probes that detect the amplified DNA may be used, again incorporating a label or other detectable moiety. The probes may bind at any suitable location in the amplicon. Probes detecting different amplified target sequences may signal at different fluorescent wavelengths to provide for multiplex detection. Dyes which intercalate with amplified DNA may also be used to detect the amplified DNA, such as SYBR green and thiazole orange.

The detection of the signal from the amplified DNA may be made by any suitable system, including real-time PCR.

Primers and Oligonucleotides

The invention further provides the primers and strand invasion oligonucleotides of SEQ ID NOs 2 to 5 and 7 to 10 and variants thereof as products per se, and compositions and formulations comprising said primers and strand invasion oligonucleotides. The primers and optionally the strand invasion oligonucleotide may be used in any method for detection of toxigenic C. difficile. Typically, the method is a strand-invasion based DNA amplification method. However, any suitable DNA amplification method that allows for specific detection of toxigenic C. difficile may be used. The upstream and downstream primers may be used in a DNA amplification method that does not require use of a strand invasion oligonucleotide, such as PCR.

Compositions and Kits

The invention also provides compositions and kits comprising at least two oligonucleotides selected from (a) an upstream primer, (b) a downstream primer and (c) a strand invasion oligonucleotide. The upstream primer, downstream primer and strand invasion oligonucleotide are as described above. The composition or kit may comprise an upstream and a downstream primer, an upstream primer and a strand invasion oligonucleotide, or a downstream primer and a strand invasion oligonucleotide. Preferably, the composition or kit comprises an upstream primer, a downstream primer and a strand invasion oligonucleotide. The composition or kit may be suitable for detection of C. difficile in accordance with the method of the invention, or an alternative DNA amplification method.

Where the composition or kit is suitable for use for detecting the target nucleic acid sequence of SEQ ID NO: 1 (tcdB), typically the upstream primer is an oligonucleotide of less than 30 nucleotides in length comprising the sequence of SEQ ID NO: 2 or a variant thereof, the downstream primer is an oligonucleotide of less than 30 nucleotides in length comprising the sequence of SEQ ID NO: 3 or a variant thereof, and the strand invasion oligonucleotide is an oligonucleotide of greater than 30 nucleotides in length comprising the sequence of SEQ ID NO: 4 or a variant thereof, and further comprising one or more modified nucleotides in its 3'region. The strand invasion oligonucleotide may have the sequence of SEQ ID NO: 5.

Where the composition or kit is suitable for use for detecting the target nucleic acid sequence of SEQ ID NO: 6 (tcdA), typically the upstream primer is an oligonucleotide of less than 30 nucleotides in length comprising the sequence of SEQ ID NO: 7 or a variant thereof, the downstream primer is an oligonucleotide of less than 30 nucleotides in length comprising the sequence of SEQ ID NO: 8 or a variant thereof, and the strand invasion oligonucleotide is an oligonucleotide of greater than 30 nucleotides in length comprising the sequence of SEQ ID NO: 9 or a variant thereof, and further comprising one or more modified nucleotides in its 3'region. The strand invasion oligonucleotide may have the sequence of SEQ ID NO: 10.

The composition or kit may provide a first set of oligonucleotides allowing for detection of the target nucleic acid sequence of SEQ ID NO: 1 and additionally a second set of oligonucleotides allowing for detection of the target nucleic acid sequence of SEQ ID NO: 6.

The above composition may be for example a solution, lyophilisate, suspension, or an emulsion in an oily or aqueous vehicle.

In the above kit, the at least two oligonucleotides may be provided as a mixture, or in separate containers. The kit optionally further comprises instructions for use in a method of the invention. The kit may comprise a means for detection of amplified DNA.

The kit or composition optionally comprises one or more probes that detect amplified DNA. The kit or composition optionally comprises one or more of a DNA polymerase, a recombinase, and recombinase accessory proteins. Preferably, the DNA polymerase is Bsu polymerase. Preferably, the recombinase is bacteriophage T4 UvsX, optionally in combination with the recombinase accessory proteins UvsY and gp32. The kit or composition may further comprise dNTPs, suitable buffers and other factors which are required for DNA amplification in the method of the invention as described above.

Diagnosis of an Infection by *C. difficile* and Medical Applications

The present invention is particularly advantageous in the medical setting. The detection methods of the invention provide a highly specific test to allow for determination of whether a clinical sample contains a target nucleic acid sequence from toxigenic *C. difficile*. The method may be applied to a range of disease settings associated with toxigenic *C. difficile*. Additionally, the method may be applied for screening of carriers of toxigenic *C. difficile*.

The determination of whether or not toxigenic *C. difficile* is present may be in the context of any disease or illness present or suspected of being present in a patient. Such diseases may include those caused by, linked to, or exacerbated by the presence of toxigenic *C. difficile*. Thus, a patient may display symptoms indicating the presence of toxigenic *C. difficile*, and a sample may be obtained from the patient in order to determine the presence of *C. difficile* and optionally also the toxinotype thereof by the method described above.

The invention thus provides a method of diagnosing an infection caused by toxigenic *C. difficile* in a subject, comprising determining the presence of a target nucleic acid sequence from toxigenic *C. difficile* according to the invention in a sample from said subject. The method may further comprise other steps of identifying the strain of toxigenic *C. difficile*, such as by microbiological culture from a sample provided by the subject.

A particularly preferred embodiment of the invention is the identification of toxigenic *C. difficile* present in patients having a gastrointestinal tract infection, in particular having symptoms of diarrhoea.

The invention thus provides a diagnostic method for gastrointestinal illnesses, such as diarrhoea that are caused by toxigenic *C. difficile*. The diagnostic method may further comprise detecting antibiotic resistance markers and virulence markers. The method provides for a dramatic improvement in the patient management of gastrointestinal illnesses because it allows for the optimal therapeutic treatment for a given patient. Thereby the test would reduce the length of hospital stays, the frequency of re-admission and reduce costs.

The diagnostic method may conveniently be performed based on nucleic acid derived from a sample of a patient, providing an indication to clinicians whether the gastrointestinal illness is due to an infection by toxigenic *C. difficile*. The diagnostic method may also provide an indication as to the toxinotype and virulence of *C. difficile* and whether the *C. difficile* is resistant to any antibiotics. Depending on the outcome of the test the medical treatment can then be optimised, for example by use of antibiotics.

The following Examples illustrate the invention.

EXAMPLES

Example 1—Design of the *C. Difficile* tcdB and tcdA Assays

Designing specific oligonucleotides for the detection and amplification of tcdA and tcdB genes was challenging. tcdA and tcdB genes show high sequence homology not only between each other but also to the other large clostridial toxins. *C. sordellii* cytotoxin gene, tcsL, is the closest homolog of tcdB (Popoff, 1987; Green, 1995). Antibodies for *C. sordellii* tcsL are cross-reactive with *C. difficile* toxin B. Thus, lateral flow tests for the detection of *C. difficile* toxin B commonly cross-react with *C. sordellii* tcsL. Design of specific oligonucleotides was further complicated by the requirement for a specific invading oligonucleotide.

Further, the GC content of *C. difficile* genome is low (29.1%) which applies also to tcdB gene, the GC content of which is 27.4%. This low GC content also made design of oligonucleotides suitable for DNA amplification challenging. Primers with low GC content will have a low melting temperature (Tm), which destabilizes binding of oligonucleotides and results in poor efficiency of amplification.

Firstly, suitable regions of the tcdA and tcdB genes were selected for targeting for detection and amplification. Particular target regions for tcdB (SEQ ID NO:1) and tcdA (SEQ ID NO: 6) are shown below. The target regions were selected 1) to be specific for *C. difficile*, i.e. to differ from closely homologous *Clostridium* species, 2) to show good inclusivity of *C. difficile* toxinotypes and 3) have a higher GC content than the *C. difficile* genome in average.

Secondly, specific oligonucleotides were designed for amplification of the target regions. Particular oligonucleotides used for detection and amplification of *C. difficile* tcdB gene and tcdA gene are shown below (SEQ ID NOs 2-5 and 7-10).

Example 2—tcdB Assay Testing tcdB detecting oligonucleotides of SEQ ID NOs 2, 3 and 5 were used to amplify *C. difficile* tcdB gene by isothermal strand invasion DNA amplification at 40° C. DNA binding fluorescent dye Sybr Green I was used for detection of amplification and fluorescence was measured either with a fluorometer or a real-time PCR instrument. The reaction mixture contained reaction buffer (10 mM Tris-acetate, pH 8, 0.5 mM EDTA, 4 mM DTT, 150 mM sucrose, 0.1 mg/ml BSA, 5% DMSO), 2 mM ATP, 5% PEG1000, 60 mM phosphocreatine di(tris) salt, dNTPs (with dTTP replaced by dUTP), 12.5 mU/μl sucrose phosphorylase, 25 mU/μl creatine phosphokinase, 62.5 mU/μl Bsu polymerase, 0.1-0.3 mg/ml T4 bacteriophage UvsX, 0.25-0.5 mg/ml T4 bacteriophage gp32, 10 mM Mg-acetate and oligonucleotides in the presence or absence of template DNA.

Figure 1A:
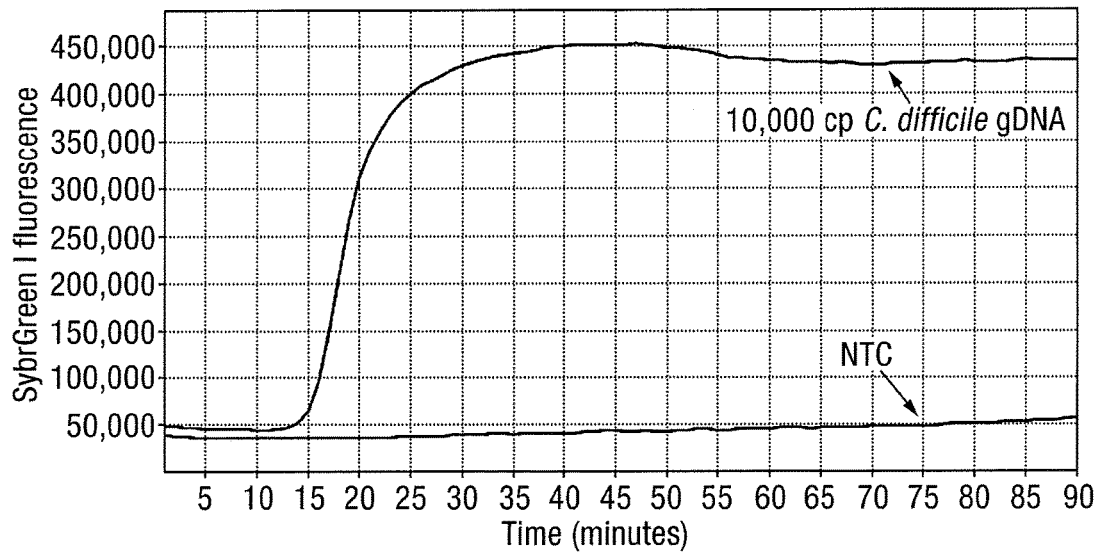
FIG. 1 shows: (A) a tcdB assay amplification plot. SybrGreen I was used for detection and fluorescence was measured with real-time PCR instrument. X-axis: time (minutes), Y-axis: SybrGreen I fluorescence (fluorescence intensity, arbitrary units). Upper trace: 10 000 genomic copies (cp) *C. difficile* BAA-1382 (630) gDNA used as template in tcdB SIBA assay. Lower trace=No template control (NTC) did not amplify. (B) Melt curve analysis of tcdB reaction. X-axis: Temperature (degrees Centigrade), Y-axis: (−d(fluorescence)/d(temperature), arbitrary units). Post-amplification melt curve analysis with SybrGreen I showed amplification of a single specific amplicon in tcdB reaction with *C. difficile* BAA-1382 (630) gDNA as template. No template control (NTC) shows no amplification. (C) Electropherogram from positive and negative tcdB reaction. X-axis: migration index (%, where lower marker is 0% and upper marker is 100%), Y-axis (fluorescence intensity, arbitrary units). Lower trace=10 000 cp *C. difficile* BAA-1382 (630) gDNA used as template in tcdB assay. Upper trace=no template control (NTC). tcdB reactions were analyzed with MultiNA microchip electrophoresis system. Only reaction oligonucleotides (rev and fwd primers and invading oligo)
Figure 1B:
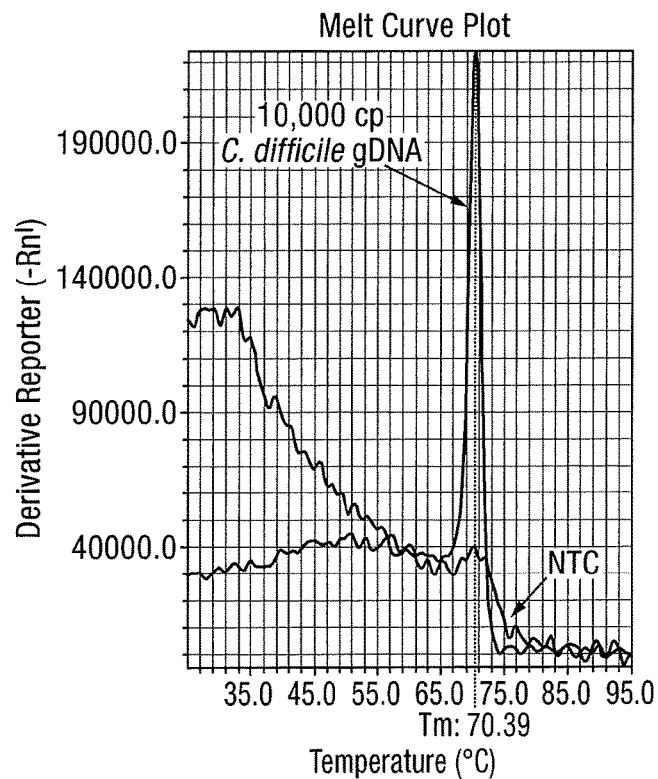

The ability of the end primers and invading oligonucleotide to produce primer-dimers or self-priming was tested in the absence of template DNA (no template control, NTC). The ability of the oligonucleotides to detect and amplify the correct target DNA was tested in the presence of *C. difficile* BAA-1382 genomic DNA (gDNA). The presence or absence of amplification product was determined both by increase in SybrGreen I fluorescence (FIG. 1(a)) and by melt curve analysis (FIG. 1(b)).

Figure 1C:
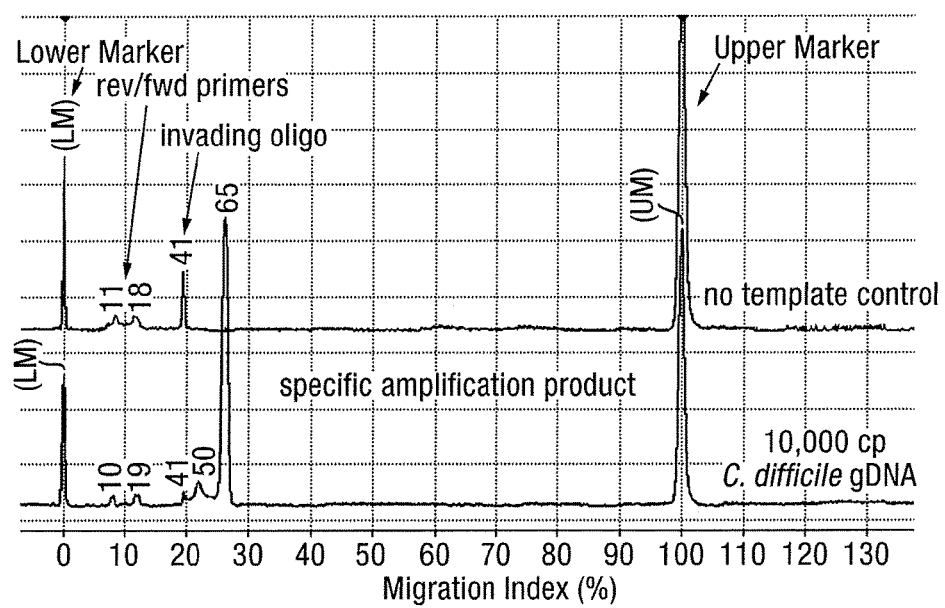

The amplification products were further analyzed with MultiNA microchip electrophoresis system (FIG. 1(c)). The electropherogram from positive tcdB amplification reaction with 10 000 copies (cp) of *C. difficile* gDNA as template showed emergence of a DNA fragment with the expected length. This fragment was not detected in the no template control reaction.

Example 3. Specificity for *C. Difficile*

Specificity of the tcdB assay was tested by using *C. sordellii* ATCC 9714 gDNA as template in a reaction as described in Example 2. *C. sordellii* toxin gene tcsL is the closest found homolog of tcdB. Results are shown in FIG. 2(a). tcdB reaction with 10 000 cp *C. sordellii* gDNA as template DNA showed no DNA amplification while 10 000 cp *C. difficile* BAA-1382 (630) showed clear amplification measured by increase in SybrGreen I fluorescence intensity.

Example 4. Sensitivity of Detection of *C. Difficile*

Sensitivity of the tcdB assay was tested with dilution series of *C. difficile* BAA-1382 (630) and amplification was measured with Sybr Green I fluorescence and detected by real-timePCR. Results are shown in FIG. 2(*b*). 10-10 000 cp/reaction *C. difficile* gDNA as template showed positive amplification whereas NTC, negative control and 1 cp/reaction did not amplify. Negative control reaction contained a mixture of isolated gDNA from *Enterobacter aerogenes, Citrobacter* sp., *Shigella sonnei, Shigella flexneri, Streptococcus agalactiae, Listeria monocytogenes, Eschericia coli, Enterobacter aerogenes, Enterobacter cloacae, Enterococcus faecalis, Citrobacter freundii* and *Klebsiella pneumoniae*, at least 1000 cp/reaction each. NTC=no template control.

Example 5. Inclusivity of Detection of *C. Difficile* Toxinotypes

Figure 3A:
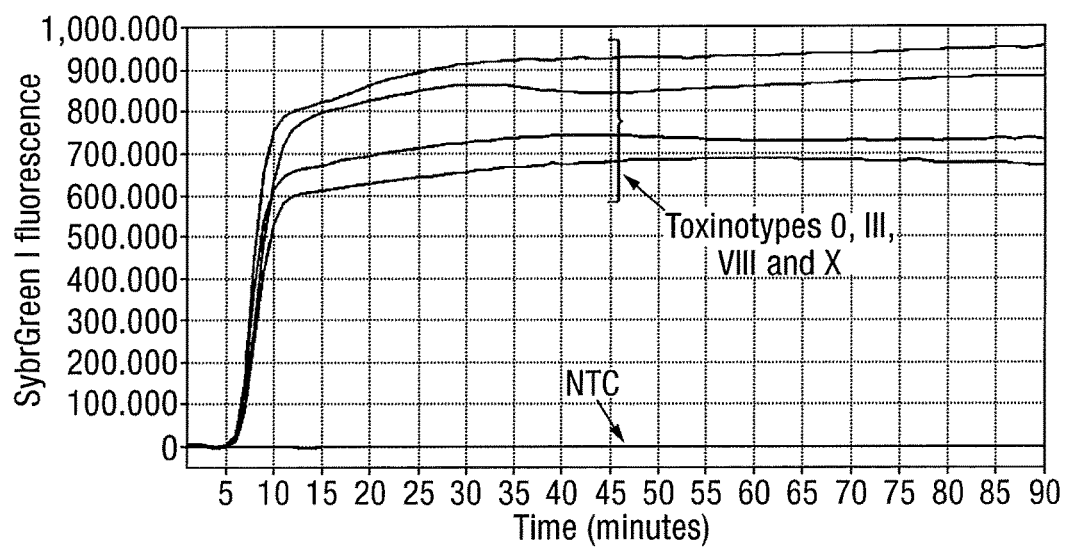
Figure 3B:
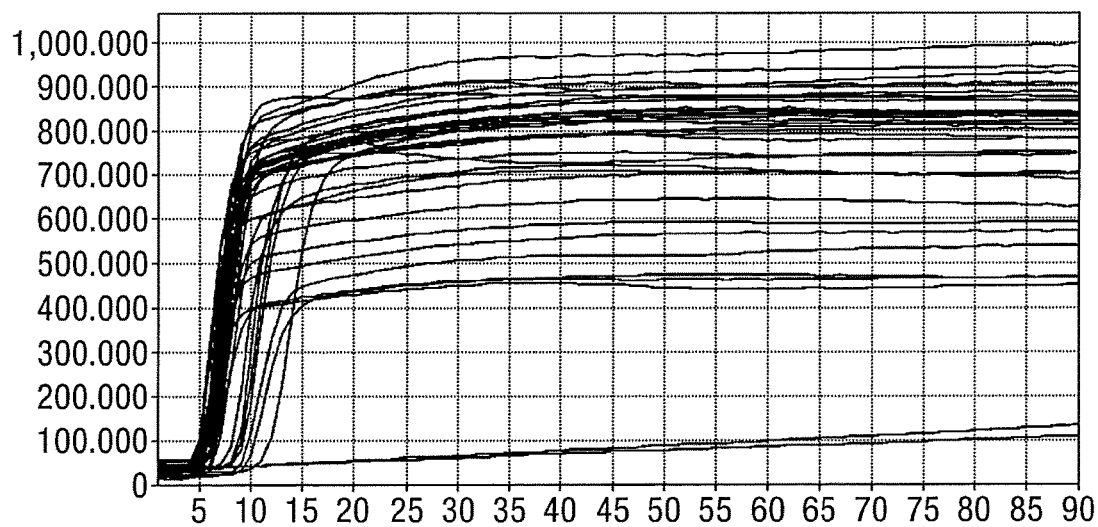
Figure 3C:
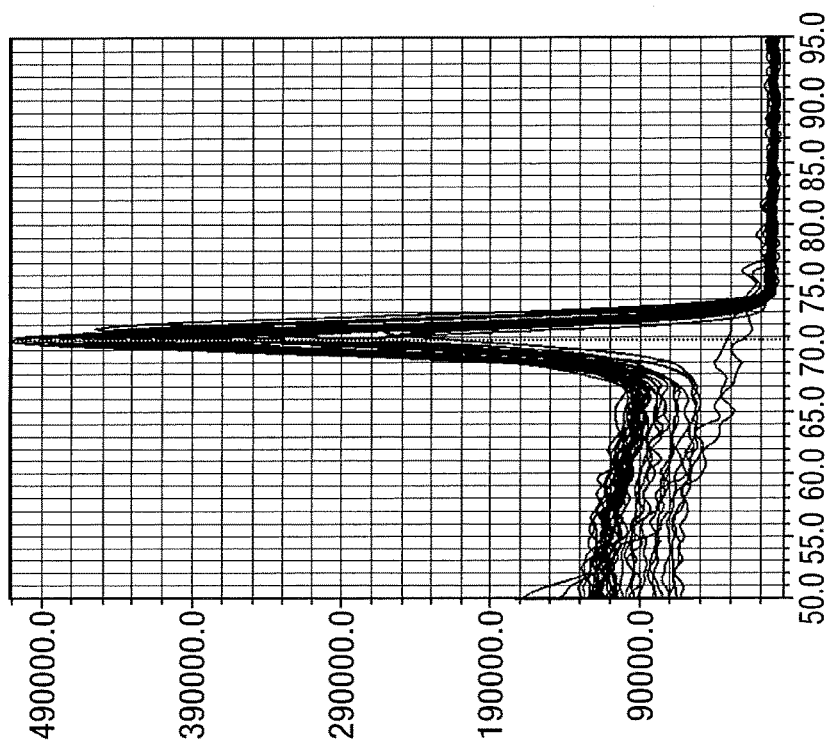
Figure 3D:
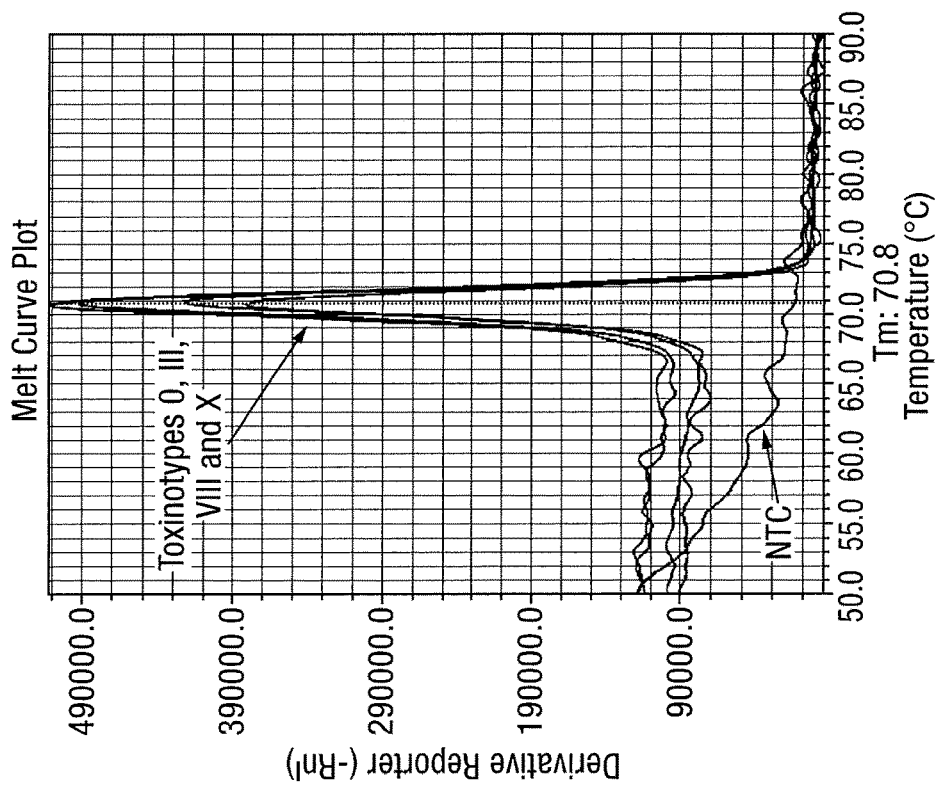

Inclusivity of the tcdB assay was tested with *C. difficile* toxinotypes 0, III, VIII and X. Results are shown in FIGS. 3(A) and (C). 2 ng gDNA/reaction from each toxinotype was used as template in the tcdB reaction. All tested toxinotypes gave a positive amplification result (FIG. 3A). Further, melt curve analysis indicated amplification of a single specific amplicon (FIG. 3C).

Inclusivity of the tcdB assay was further tested with a larger panel of 37 *C. difficile* Toxinotypes 0, I, II, IIIa, IIIb, IIIc, IV, V, VI, VII, VIII, IX, X, XIa, XIb, XII, XIII, XIV, XV, XVI, XVII, XVIII; XIX, XX, XXI; XXII; XXIII; XXIV, XXV, XXVI, XXVII, XVIII, XXIX, XXX, XXXI, XXXII and XXXIII. Results are shown in FIGS. 3(B) and (D). All toxinotypes except for XIa and XIb, 35 in total, gave a positive amplification result (FIG. 3(B), and post-amplification melt curve analysis from positive amplification reactions showed amplification of a single amplicon (FIG. 3(C)). Post-amplification melt curve analysis for toxinotypes XIa and XIb also showed no amplification. The negative amplification for toxinotypes XIa and XIb is expected as these do not produce either toxin A or toxin B (Rupnik et al. 2001). They lack tcdB gene completely but contain at least some parts of tcdA gene.

Figure 4B:
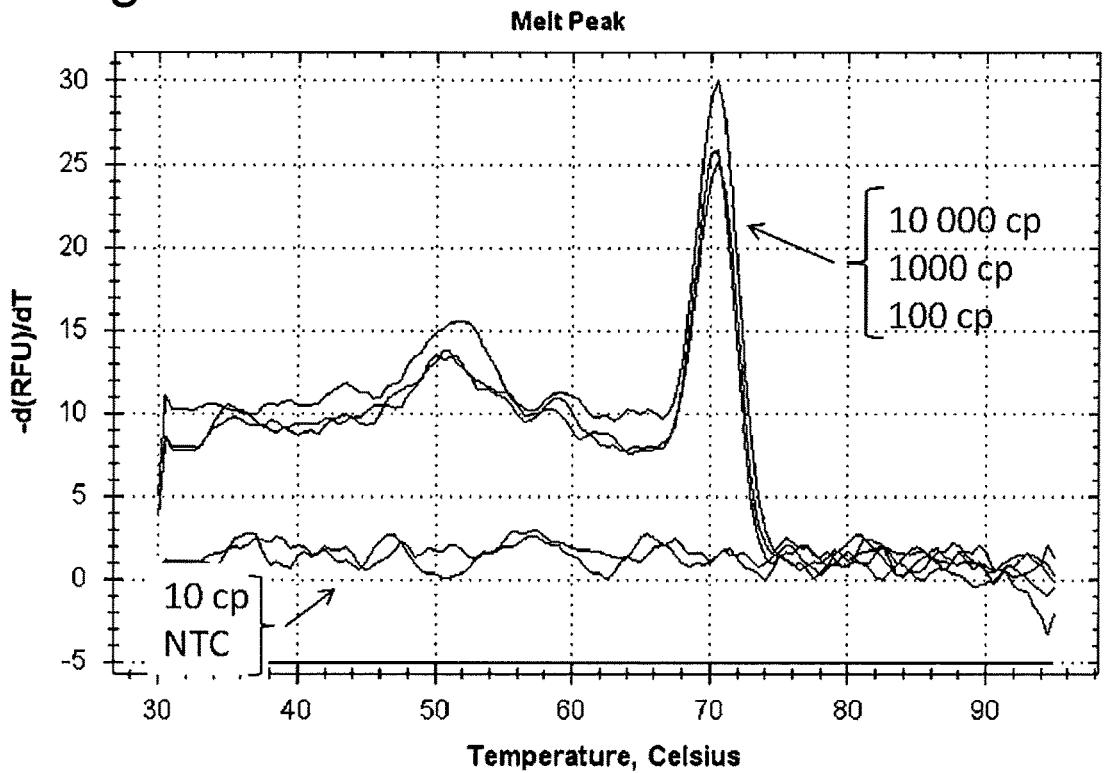

Example 6. tcdA SIBA Assay Testing tcdA detecting oligonucleotides of SEQ ID NOs 7, 8 and 10 were used to amplify *C. difficile* tcdA gene at 40° C. with a reaction mixture as described in Example 1. The ability of the end primers to produce primer-dimers or self-priming was tested in the absence of template DNA (no template control, NTC). The ability of the oligonucleotides to detect and amplify the correct target DNA was tested in the presence of 10-10 000 cp/reaction *C. difficile* BAA-1382 genomic DNA (gDNA). The presence or absence of amplification product was determined by increase in SybrGreen I fluorescence (FIG. 4*a*) and measured with real-time PCR instrument. Melt curve analysis was performed to confirm amplification of single specific amplicon (FIG. 4*b*).

Sequences of the Invention

```
SEQ ID NO: 1
AACCAAAGTGGAGTGTTACAAACAGGTGTATTTAGTACAGAAGATGG
ATTTAAATATTTTGCCCCA

SEQ ID NO: 2 AACCAAAGTGGAGTGTTACAA

SEQ ID NO: 3 TGGGGCAAAATATTTA

SEQ ID NO: 4 TCCTCCTGTACCTCGTTACAAACAGGTGTATTTA
GTACAGAAGATGGATTTAAATA

SEQ ID NO: 5
TCCTCCTGTACCTCGTTACAAACAGGTGTATTTAGTACAGAAGmAm
UmGmGmAmUmUmAmAmAmUmA/
InvdT/.mX = 2'-O-
methyl RNA. invdT = inverted dTTP.

SEQ ID NO: 6
ATGGATAGGTGGAGAAGTCAGTGATATTGCTCTTGAATACATAAAA
CAATGGGCTGATATTAA

SEQ ID NO: 7 ATGGATAGGTGGAGAAGTC

SEQ ID NO: 8 TTAATCTCAGCCCATTG

SEQ ID NO: 9 TCCTCCTGTACCTCAGAAGTCAGTGATATTGCTC
TTGAATACATAAAACAATGG

SEQ ID NO: 10
TCCTCCTGTACCTCAGAAGTCAGTGATATTGCTCTTGAATmAmCmAm
UmAmAmAmAmCmAmAmUmGmG/InvdT/.mX = 2'-O-
methyl RNA. invdT = inverted dTTP.
```

REFERENCES

Braun, V., Hundsberger, T., Leukel, P., Sauerborn, M. and von Eichel-Streiber, C. (1996) Definition of the single integration site of the pathogenicity locus in *Clostridium difficile*. Gene 181 (1-2): 29-38

Carter, G. P., Rood, J. I. and Lyras, D. (2012) The role of toxin A and toxin B in the virulence of *Clostridium difficile*. Trends in Microbiology 20(1): 21-29

Green, G. A., Schué, V. and Monteil, H. (1995) Cloning and characterization of the cytotoxin L-encoding gene of *clostridium sordellii*: homology with *clostridium difficile* cytotoxin B. Gene 161(1): 57-61

Lyras, D., O'Connor, J., Howarth, P. M., Sambol, S. P., Carter, G. P., Phumoonna, T., Poon, R., Adams, V., Vedantam, G., Johnson, S., Gerding, D. N., and Rood, J. I. (2009) Toxin B is essential for virulence of *Clostridium difficile*. Nature 458(7242): 1176-1179

McMillin, D. E., Muldrow, L. L. and Laggette, S. J. (1990) Simultaneous detection of toxin A and toxin B genetic determinants of *Clostridium difficile* using the multiplex polymerase chain reaction. Canadian journal of microbiology 38(1), 81-83.

McMillin, D. E., Muldrow, L. L., Leggette, S. J., Abdulahi, Y. and Ekanemesang, U. M. (1991) Molecular screening of *Clostridium difficile* toxins A and B genetic determinants and identification of mutant strains. FEMS Microbiology Letters 62(1):75-80.

Popoff, M. R. (1987) Purification and characterization of *Clostridium sordellii* lethal toxin and cross-reactivity with *Clostridium difficile* cytotoxin. Infect. Immun. 55(1): 35-43

Rupnik, M., Brazier, J. S., Duerden, B. I., Grabnar, M. and Stubbs, S. L. J. (2001) Comparison of toxinotyping and PCR ribotyping of *Clostridium difficile* strains and description of novel toxinotypes Microbiology 147, 439-447.

von Eichel-Streiber, C., Boquet, P., Sauerborn, M. and Thelestam, M. (1996) Large clostridial cytotoxins—a family of glycosyltransferases modifying small GTP-binding proteins. Trends in Microbiology 4: 375-382

Wren, B. W., Clayton, C. L. and Tabaqchali, S. (1990) Nucleotide sequence of *Clostridium difficile* toxin A gene fragment and detection of toxigenic strains by polymerase chain reaction. FEMS Microbiology Letters 58(1), 1-6

The invention claimed is:

1. A method for detecting a target nucleic acid sequence of toxigenic C. difficile in a sample, said method comprising:
   contacting said sample with at least one upstream primer, at least one downstream primer and at least one strand invasion oligonucleotide under conditions suitable for amplification by strand invasion of said target nucleic acid sequence,
   wherein each said primer and said strand invasion oligonucleotide comprises a region complementary to said target nucleic acid sequence;
   wherein said strand invasion oligonucleotide renders at least a portion of the target nucleic acid sequence single-stranded to allow the binding of said upstream primer and said downstream primer; and
   wherein said upstream primer is an oligonucleotide of less than 30 nucleotides in length comprising the sequence of SEQ ID NO: 2 or a variant thereof having at least 70% sequence identity to the sequence of SEQ ID NO: 2, wherein said downstream primer is an oligonucleotide of less than 30 nucleotides in length comprising the sequence of SEQ ID NO: 3 or a variant thereof having at least 70% sequence identity to the sequence of SEQ ID NO: 3, and wherein said strand invasion oligonucleotide is of the sequence of SEQ ID NO: 5; and
   assaying for amplification of the target nucleic acid sequence, said amplification being indicative of the presence of the target nucleic acid sequence of toxigenic C. difficile in the sample.

2. A method for detecting a target nucleic acid sequence of toxigenic C. difficile in a sample, said method comprising:
   contacting said sample with at least one upstream primer, at least one downstream primer and at least one strand invasion oligonucleotide under conditions suitable for amplification by strand invasion of said target nucleic acid sequence,
   wherein each said primer and said strand invasion oligonucleotide comprises a region complementary to said target nucleic acid sequence;
   wherein said strand invasion oligonucleotide renders at least a portion of the target nucleic acid sequence single-stranded to allow the binding of said upstream primer and said downstream primer; and
   wherein said upstream primer is an oligonucleotide of less than 30 nucleotides in length comprising the sequence of SEQ ID NO: 7 or a variant thereof having at least 70% sequence identity to the sequence of SEQ ID NO: 7, wherein said downstream primer is an oligonucleotide of less than 30 nucleotides in length comprising the sequence of SEQ ID NO: 8 or a variant thereof having at least 70% sequence identity to the sequence of SEQ ID NO: 8, and wherein said strand invasion oligonucleotide is of the sequence of SEQ ID NO: 10; and
   assaying for amplification of the target nucleic acid sequence, said amplification being indicative of the presence of the target nucleic acid sequence of toxigenic C. difficile in the sample.

3. A method according to claim 1 wherein the variant of the upstream primer comprises a sequence having 1, 2, 3 or 4 mismatches to the sequence of SEQ ID NO:2 and the variant of the downstream primer comprises a sequence having 1, 2, 3 or 4 mismatches to the sequence of SEQ ID NO:3.

4. A method according to claim 2 wherein the variant of the upstream primer comprises a sequence having 1, 2, 3 or 4 mismatches to the sequence of SEQ ID NO: 7 and the variant of the downstream primer comprises a sequence having 1, 2, 3 or 4 mismatches to the sequence of SEQ ID NO: 8.

5. A method according to claim 1 or 2, which further comprises contacting of said sample with a recombinase.

6. A method according to claim 1 or 2, which is carried out under isothermal conditions promoting amplification of said target nucleic acid sequence.

7. A method according to claim 1 or 2 wherein the at least one upstream primer, at least one downstream primer and at least one strand invasion oligonucleotide are provided as part of a kit.

* * * * *

```
                         SEQUENCE LISTING

<160> NUMBER OF SEQ ID NOS: 10

<210> SEQ ID NO 1
<211> LENGTH: 66
<212> TYPE: DNA
<213> ORGANISM: Artificial Sequence
<220> FEATURE:
<223> OTHER INFORMATION: TARGET REGION

<400> SEQUENCE: 1
aaccaaagtg gagtgttaca aacaggtgta tttagtacag aagatggatt taaatatttt      60
gcccca                                                                66

<210> SEQ ID NO 2
<211> LENGTH: 21
<212> TYPE: DNA
<213> ORGANISM: Artificial Sequence
<220> FEATURE:
<223> OTHER INFORMATION: PRIMER SEQUENCE

<400> SEQUENCE: 2
aaccaaagtg gagtgttaca a                                               21

<210> SEQ ID NO 3
<211> LENGTH: 16
<212> TYPE: DNA
<213> ORGANISM: Artificial Sequence
<220> FEATURE:
<223> OTHER INFORMATION: PRIMER SEQUENCE

<400> SEQUENCE: 3
tggggcaaaa tattta                                                     16

<210> SEQ ID NO 4
<211> LENGTH: 56
<212> TYPE: DNA
<213> ORGANISM: Artificial Sequence
<220> FEATURE:
<223> OTHER INFORMATION: STRAND INVADING OLIGONUCLEOTIDE

<400> SEQUENCE: 4
tcctcctgta cctcgttaca aacaggtgta tttagtacag aagatggatt taaata         56

<210> SEQ ID NO 5
<211> LENGTH: 56
<212> TYPE: DNA
<213> ORGANISM: Artificial Sequence
<220> FEATURE:
<223> OTHER INFORMATION: MODIFIED STRAND INVADING OLIGONUCLEOTIDE
<220> FEATURE:
<221> NAME/KEY: misc_feature
<222> LOCATION: (44)..(44)
<223> OTHER INFORMATION: 2'-O-METHYL RNA
<220> FEATURE:
<221> NAME/KEY: misc_feature
<222> LOCATION: (45)..(45)
<223> OTHER INFORMATION: 2'-O-METHYL RNA
<220> FEATURE:
<221> NAME/KEY: misc_feature
<222> LOCATION: (46)..(46)
<223> OTHER INFORMATION: 2'-O-METHYL RNA
<220> FEATURE:
<221> NAME/KEY: misc_feature
```

```
<222> LOCATION: (47)..(47)
<223> OTHER INFORMATION: 2'-O-METHYL RNA
<220> FEATURE:
<221> NAME/KEY: misc_feature
<222> LOCATION: (48)..(48)
<223> OTHER INFORMATION: 2'-O-METHYL RNA
<220> FEATURE:
<221> NAME/KEY: misc_feature
<222> LOCATION: (49)..(49)
<223> OTHER INFORMATION: 2'-O-METHYL RNA
<220> FEATURE:
<221> NAME/KEY: misc_feature
<222> LOCATION: (50)..(50)
<223> OTHER INFORMATION: 2'-O-METHYL RNA
<220> FEATURE:
<221> NAME/KEY: misc_feature
<222> LOCATION: (51)..(51)
<223> OTHER INFORMATION: 2'-O-METHYL RNA
<220> FEATURE:
<221> NAME/KEY: misc_feature
<222> LOCATION: (52)..(52)
<223> OTHER INFORMATION: 2'-O-METHYL RNA
<220> FEATURE:
<221> NAME/KEY: misc_feature
<222> LOCATION: (53)..(53)
<223> OTHER INFORMATION: 2'-O-METHYL RNA
<220> FEATURE:
<221> NAME/KEY: misc_feature
<222> LOCATION: (54)..(54)
<223> OTHER INFORMATION: 2'-O-METHYL RNA
<220> FEATURE:
<221> NAME/KEY: misc_feature
<222> LOCATION: (54)..(54)
<223> OTHER INFORMATION: 2'-O-METHYL RNA
<220> FEATURE:
<221> NAME/KEY: misc_feature
<222> LOCATION: (55)..(55)
<223> OTHER INFORMATION: 2'-O-METHYL RNA
<220> FEATURE:
<221> NAME/KEY: misc_feature
<222> LOCATION: (56)..(56)
<223> OTHER INFORMATION: INVERTED dTTP

<400> SEQUENCE: 5
tcctcctgta cctcgttaca aacaggtgta tttagtacag aagauggauu uaaaun        56

<210> SEQ ID NO 6
<211> LENGTH: 63
<212> TYPE: DNA
<213> ORGANISM: Artificial Sequence
<220> FEATURE:
<223> OTHER INFORMATION: TARGET REGION

<400> SEQUENCE: 6
atggataggt ggagaagtca gtgatattgc tcttgaatac ataaaacaat gggctgatat    60
taa                                                                  63

<210> SEQ ID NO 7
<211> LENGTH: 19
<212> TYPE: DNA
<213> ORGANISM: Artificial Sequence
<220> FEATURE:
<223> OTHER INFORMATION: PRIMER SEQUENCE

<400> SEQUENCE: 7
atggataggt ggagaagtc                                                 19

<210> SEQ ID NO 8
<211> LENGTH: 17
<212> TYPE: DNA
<213> ORGANISM: Artificial Sequence
<220> FEATURE:
```

<223> OTHER INFORMATION: PRIMER SEQUENCE

<400> SEQUENCE: 8
ttaatctcag cccattg                                                          17

<210> SEQ ID NO 9
<211> LENGTH: 54
<212> TYPE: DNA
<213> ORGANISM: Artificial Sequence
<220> FEATURE:
<223> OTHER INFORMATION: STRAND INVADING OLIGONUCLEOTIDE

<400> SEQUENCE: 9
tcctcctgta cctcagaagt cagtgatatt gctcttgaat acataaaaca atgg                 54

<210> SEQ ID NO 10
<211> LENGTH: 55
<212> TYPE: DNA
<213> ORGANISM: Artificial Sequence
<220> FEATURE:
<223> OTHER INFORMATION: STRAND INVADING OLIGONUCLEOTIDE
<220> FEATURE:
<221> NAME/KEY: misc_feature
<222> LOCATION: (41)..(41)
<223> OTHER INFORMATION: 2'-O-METHYL RNA
<220> FEATURE:
<221> NAME/KEY: misc_feature
<222> LOCATION: (42)..(42)
<223> OTHER INFORMATION: 2'-O-METHYL RNA
<220> FEATURE:
<221> NAME/KEY: misc_feature
<222> LOCATION: (43)..(43)
<223> OTHER INFORMATION: 2'-O-METHYL RNA
<220> FEATURE:
<221> NAME/KEY: misc_feature
<222> LOCATION: (44)..(44)
<223> OTHER INFORMATION: 2'-O-METHYL RNA
<220> FEATURE:
<221> NAME/KEY: misc_feature
<222> LOCATION: (45)..(45)
<223> OTHER INFORMATION: 2'-O-METHYL RNA
<220> FEATURE:
<221> NAME/KEY: misc_feature
<222> LOCATION: (46)..(46)
<223> OTHER INFORMATION: 2'-O-METHYL RNA
<220> FEATURE:
<221> NAME/KEY: misc_feature
<222> LOCATION: (47)..(47)
<223> OTHER INFORMATION: 2'-O-METHYL RNA
<220> FEATURE:
<221> NAME/KEY: misc_feature
<222> LOCATION: (48)..(48)
<223> OTHER INFORMATION: 2'-O-METHYL RNA
<220> FEATURE:
<221> NAME/KEY: misc_feature
<222> LOCATION: (49)..(49)
<223> OTHER INFORMATION: 2'-O-METHYL RNA
<220> FEATURE:
<221> NAME/KEY: misc_feature
<222> LOCATION: (50)..(50)
<223> OTHER INFORMATION: 2'-O-METHYL RNA
<220> FEATURE:
<221> NAME/KEY: misc_feature
<222> LOCATION: (51)..(51)
<223> OTHER INFORMATION: 2'-O-METHYL RNA
<220> FEATURE:
<221> NAME/KEY: misc_feature
<222> LOCATION: (52)..(52)
<223> OTHER INFORMATION: 2'-O-METHYL RNA
<220> FEATURE:
<221> NAME/KEY: misc_feature
<222> LOCATION: (53)..(53)
<223> OTHER INFORMATION: 2'-O-METHYL RNA
<220> FEATURE:
<221> NAME/KEY: misc_feature

```
<222> LOCATION: (54)..(54)
<223> OTHER INFORMATION: 2'-O-METHYL RNA
<220> FEATURE:
<221> NAME/KEY: misc_feature
<222> LOCATION: (55)..(55)
<223> OTHER INFORMATION: INVERTED dTTP

<400> SEQUENCE: 10
tcctcctgta cctcagaagt cagtgatatt gctcttgaat acauaaaaca auggn         55
```